United States Patent [19]

Lystager

[11] Patent Number: 5,655,957
[45] Date of Patent: Aug. 12, 1997

[54] SHARPENING MACHINE

[76] Inventor: Gregers Lystager, Holmevej 10, DK-2830 Virum, Denmark, DK-2830

[21] Appl. No.: 591,683

[22] PCT Filed: Aug. 22, 1994

[86] PCT No.: PCT/DK94/00315

§ 371 Date: Feb. 23, 1996

§ 102(e) Date: Feb. 23, 1996

[87] PCT Pub. No.: WO95/05920

PCT Pub. Date: Mar. 2, 1995

[30] Foreign Application Priority Data

Aug. 27, 1993 [DK] Denmark ................. 0973/93

[51] Int. Cl.⁶ ..................... B24B 7/00; B24B 9/00
[52] U.S. Cl. ............. 451/278; 451/382; 451/549; 451/45
[58] Field of Search ................. 451/278, 282, 451/45, 293, 382, 549, 409

[56] References Cited

U.S. PATENT DOCUMENTS

| | | | |
|---|---|---|---|
| 1,556,471 | 10/1925 | Andrus | 451/549 |
| 2,264,598 | 12/1941 | Stainbrook | 451/382 |
| 2,271,810 | 2/1942 | Waldron | 451/278 |
| 2,578,309 | 12/1951 | Kroczek | 451/278 |
| 4,773,186 | 9/1988 | Kojima | 451/278 |
| 5,197,227 | 3/1993 | Svanberg | 451/278 |
| 5,331,774 | 7/1994 | Domenella | 451/45 |

*Primary Examiner*—Robert A. Rose
*Assistant Examiner*—George Nguyen
*Attorney, Agent, or Firm*—Ray F. Cox, Jr.

[57] ABSTRACT

A sharpening machine for sharpening the cutting edges of instruments, particularly the curved inner cutting edges of dental instruments, to obtain an arbitrary wedge angle. A grinding disk is provided with both a plane surface and a radiused outer edge. A shaft extension extends above the plane of the grinding disk and serves to support the instrument as it is being sharpened. The longitudinal axis of the instrument is displaced away from the axis of rotation of the shaft extension by an offset one-half distance equal to the diameter of the shaft extension thereby determining an offset angle of the longitudinal axis of the instrument with respect to the grinding disk and thus the wedge angle of sharpening of the curved inner edge of the instrument. In order to facilitate the sharpening of the curved inner edge of the instrument, the outer edge of the grinding disk is formed with a radius shorter than the radius of curvature of the instrument.

7 Claims, 6 Drawing Sheets

1

SHARPENING MACHINE

BACKGROUND OF THE INVENTION

The invention refers to an apparatus of the in the introduction of claim 1 described type. From the U.S. patent application Ser. No. 1,556,471 a similar apparatus is known. This well-known apparatus is suitable for sharpening the edges of instruments with outer cutting edges. However, it is not possible to sharpen instruments with inner, curved cutting edges of different cutting angles. The reproduction of the outer grinding angles is also doubtful, as it is not stated where to place the cutting edge on the grinding disk during the grinding process. The requirements of hygiene in connection with e.g. dental intruments cannot be met by this well-known technique, either. The purpose of the invention is to present an apparatus of the above mentioned well-known type, but by which the disadvantages of the well-known technique are rectified.

SUMMARY OF THE INVENTION

According to the invention this is obtained by an apparatus, which is characteristic of what is stated in the characterizing part of Claim 1.

By designing the apparatus this way the adjustment of the distance of the instrument from the axis of rotation makes it possible to grind the inner cutting edge by an arbitrary wedge angle.

By designing the extended axle, as described in Claim 2, a support is obtained, by which a specific wedge angle can be reproduced very simply by choosing a suitable diameter of the shaft extension.

The in Claim 3 described design makes it possible to extend the axle of the grinding disk in a very simple way.

By designing the apparatus as described in Claim 4, the entire parts of the apparatus can be dismounted to be sterilized and remounted in a simple way.

The in Claim 5 described design of the grinding disk is especially advantegeous, because it ensures an acceptable rotation without twisting (uneven running), which is very important especially for dental instruments with inner cutting edges. By removal of tartar and smoothening of root cement it is important that the cutting edge is sharp and regular with no cuts or grinding checks.

The in Claim 6 described placement of the instrument above the diagonal line of the grinding disk makes it possible with close accuracy of repetition to sharpen the cutting edge of the outer sharpened facet.

The in Claim 7 described design makes it possible to start the grinding process very advantegeously without touching the apparatus itself. Consequently, the risk of contamination is minimized, when the grinding process is carded out during the treatment of patients.

BRIEF DESCRIPTION OF THE DRAWINGS

The invention will be further explained below, with reference to the drawings, described in the following.

DESCRIPTION OF THE PREFERRED EMBODIMENTS

Figure 1:
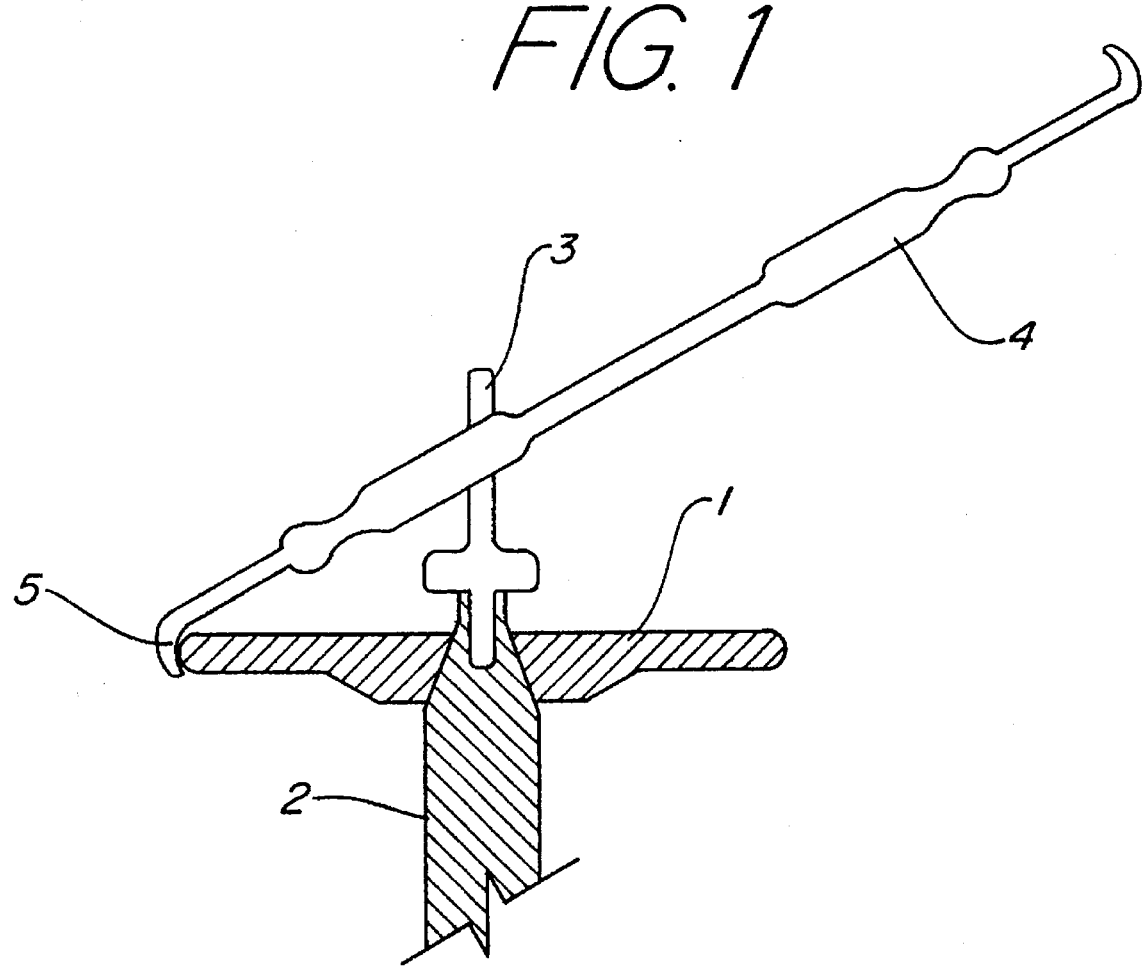
FIG. 1 shows grinding disk mounted on the driving shaft, displayed from the side with an shaft extension, which is to set off the instrument in relation to the diagonal line of the grinding disk.
Figure 3:
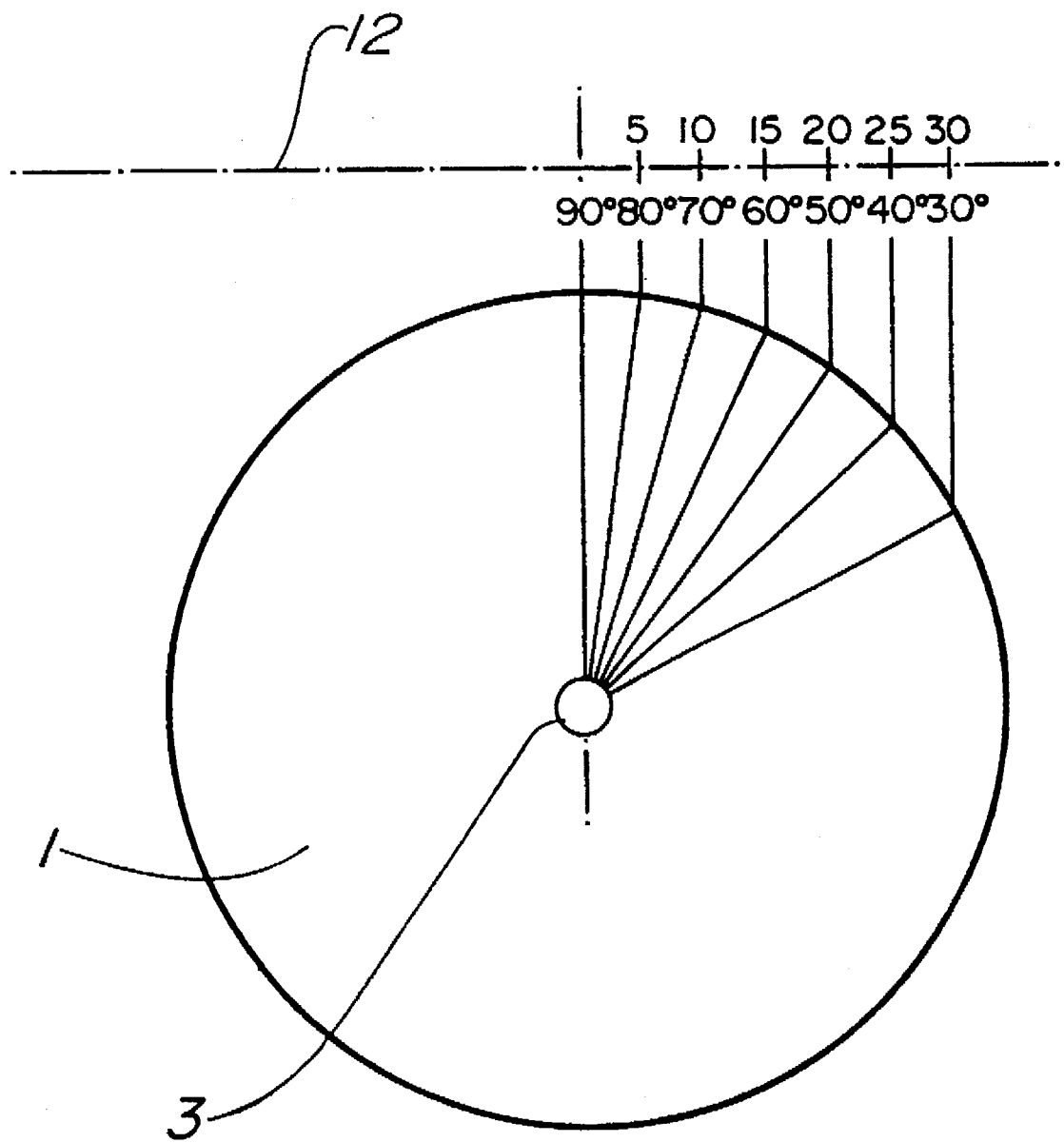
FIG. 3 shows the grinding disk seen from above with the extended axle, providing the offset angle in relation to the diagonal angle. The larger displacement, the larger angle.

The shaft extension 3 is shown in FIGS. 1, 3, 4, and 5. Particularly, with respect to FIG. 1, the grinding disk 1 is shown mounted on the driving shaft 2. The shaft extension 3 extends above the plane surface of the grinding disk 1, and with its axis aligned with the axis of the driving shaft 2 as shown by FIGS. 1 and 3.

FIG. 1 shows the axle extension 3 used to support an instrument at an angle to the plane surface of the grinding disk 1 so that the curved radius 6 on the periphery of the grinding disk 1 contacts the inner cutting edge of the instrument 4. (See also FIG. 2). The exact manner in which the instrument 4 is held to the axle extension 3 is not shown but mechanical supports for instruments being sharpened on a grinding disk are well known in the art and the provision of such a support would be within the capabilities of one skilled in the art. It should also be noted that the present invention does not require the provision of any type of fixed mechanical support for attaching or supporting the instrument 4 on the axle extension 3. The axle extension 3 may provide a support simply by allowing the instrument 4 to be manually rested against the axle extension 3 during a sharpening operation as shown in FIG. 1.

The wedge angle or cutting angle 5 is shown by FIG. 3. As explained previously on page 1, lines 18–20, the wedge angle 5 is simply the angle to which the inner cutting edge of the instrument 4 is sharpened. As shown in FIG. 1, and in detail in FIG. 2, the curved inner cutting edge of the instrument 4 is placed in contact with the curved outer radius 6 on the periphery of the grinding disk 1 to sharpen the instrument 4 to the arbitrary wedge angle 5 on the curved inner cutting edge of the instrument 4.

If the longitudinal axis of the instrument 4 were aligned radially outward from the center of the axle extension 3 to the periphery of the grinding disk 1, then the wedge angle 5 would be at 90 degrees to the radial line from the center of the axle extension 3 since the periphery of the grinding disk 1 necessarily sharpens by grinding a surface on the instrument 4 tangent to the periphery of the grinding disk 1. In order to obtain other wedge angles 5, some means is required to angularly offset the instrument 4 with respect to the radial line from the center of the axle extension 3. In the present invention, this offset is provided by the diameter of the axle extension 3 as shown in FIG. 3. In FIG. 3, a radial line from the center of the axle extension 3 to the periphery of the grinding disk is shown with the legend "90 degrees." In other words, when the longitudinal axis of the instrument 4 is aligned (viewed vertically) with the radial line from the center of the axle extension 3, the wedge angle 5 is 90 degrees. However, when the instrument 4 is placed against the axle extension 3 without changing the position of the cutting edge of the instrument 4 against the periphery of the grinding disk 1, an offset angle of the instrument 4 with respect to the radial line is produced, and thus the wedge angle 5 is altered. The greater the diameter of the axle extension 3, the greater the offset distance and therefore the greater the offset angle which produces a proportionate change in the wedge angle 5 as shown in the series of numbers in FIG. 3.

Figure 2:
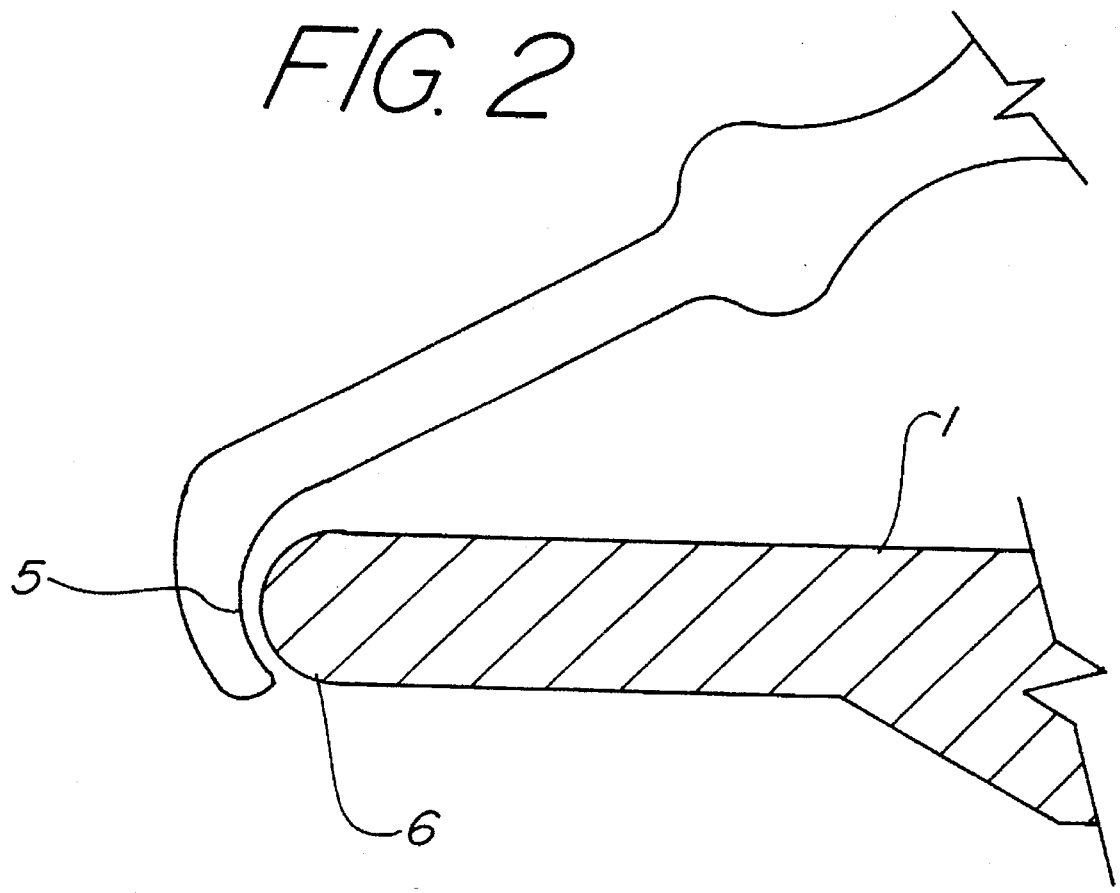
FIG. 2 shows that the radius of the grinding disk is shorter than the radius of curvature of the instrument.

It should be understood that a typical dental instrument of the type which may be sharpened by the present invention has a curved tip as shown in FIGS. 1 and 2. The curved tip has a curved inner cutting surface or face which may be sharpened on the present invention to a wedge angle 5. This sharpening operation as shown on FIGS. 1, 2, and 3 is performed by placing the curved inner cutting surface in contact with the curved outer periphery of the grinding disk 1. As noted above, placing the dental instrument 4 so that its longitudinal axis is aligned with a radius of the grinding disk 1 would necessarily result in the curved inner face of the tip of the instrument 4 being sharpened flat; i.e., to a wedge angle of 90 degrees with respect to the longitudinal axis of the instrument 4. This is the result since the angle to which the curved inner face is sharpened is the direct result of holding the curved inner face of the tip of the instrument 4 against the periphery of the grinding disk 1 which produces a wedge angle on the instrument 4 tangent to the periphery of the grinding disk 1. To produce other wedge angles 5 it is necessary to offset the instrument 4 in some manner so that the curved inner face of the instrument contacts the periphery of the grinding disk 1 at another angle. In the present invention this is accomplished using an axle extension 3 of the driving shaft 2 to form a guide to determine specific offsets.

The axle extension 3 acts as a guide in the following manner. The axle extension 3 is an extension of the driving shaft 2 and rotates on the same axis as the center of the grinding disk 1. The axle extension 3 is removable and may be of various diameters. With the axle extension removed, the curved inner face of the tip of the instrument 4 may be sharpened by placing the curved inner face against the periphery of the grinding disk 1. If the instrument is placed so that the longitudinal axis of the instrument is aligned with a radius of the grinding disk 1, then the curved inner face is necessarily sharpened to a tangent to the periphery of the grinding disk 1, which is a wedge angle 5 of 90 degrees to the longitudinal axis of the instrument 4. The instrument 4 may be held in this alignment by various means which are not critical to the operation of the present invention and which would be within the capabilities of those skilled in the art. For example, a skilled operator could manually place the instrument by eye in the appropriate alignment using the axle extension to support the instrument. Alternatively, a rest or guide of the type found in the prior art could be employed.

Sharpening the curved inner face of the instrument 4 to another angle may be described with reference to FIG. 3. Consider an axle extension 3 of arbitrary diameter placed on the grinding disk 1 and extending upwardly from the surface of the grinding disk 1. If the instrument 4 is placed against the axle extension as shown in FIG. 1 and held so that the longitudinal axis of the instrument 4 is parallel to a radius of the grinding disk 1, then when the curved inner face of the tip of the instrument 4 is placed against the periphery of the grinding disk 1, the tangent to the periphery of the grinding disk 1 is no longer at 90 degrees to the longitudinal axis of the instrument 4. This is due to the longitudinal axis being displaced away from the center of the grinding disk 1 by a distance equal to one-half of the diameter of the axle extension 3.

FIG. 3 provides an illustration showing how various diameters of the axle extension (half the diameter of the axle extension equals the "offset distance" from the axis of rotation) each produce a particular offset angle in the alignment of the instrument and thus a particular angle with respect to a tangent to the periphery of the grinding disk.

In FIG. 3, a radial line from the center of the axle extension 3 to the periphery of the grinding 1 disk is shown with the legend "90 degrees." In other words, when the longitudinal axis of the instrument 4 is aligned (viewed vertically) with the radial line from the center of the axle extension 3, the wedge angle 5 is 90 degrees. The offset distance or offset angle 12 is illustrative of the effect of offsetting the instrument 4 from the center of rotation of the grinding disk 1. The numbers 5–30 are simply indicative of relative offset distances to illustrate that greater offset distances; i.e., greater half diameters of the axle extension, produce greater offset angles with respect to a tangent to the periphery of the grinding disk 1. The absolute meaning of the offset distances and the offset angles are not significant to the meaning and scope of the present invention. What is significant is the concept that the axle extension 3 (through the selection of a particular diameter) provides a means to produce an offset of the instrument 4 from an orientation along the radius of the grinding disk 1 and therefore a simple and reproducible means of selecting a particular orientation of the cutting edge of the instrument with respect to a tangent to the periphery of the grinding disk 1 and therefore a particular wedge angle 5 for grinding the cutting edge.

Figure 4:
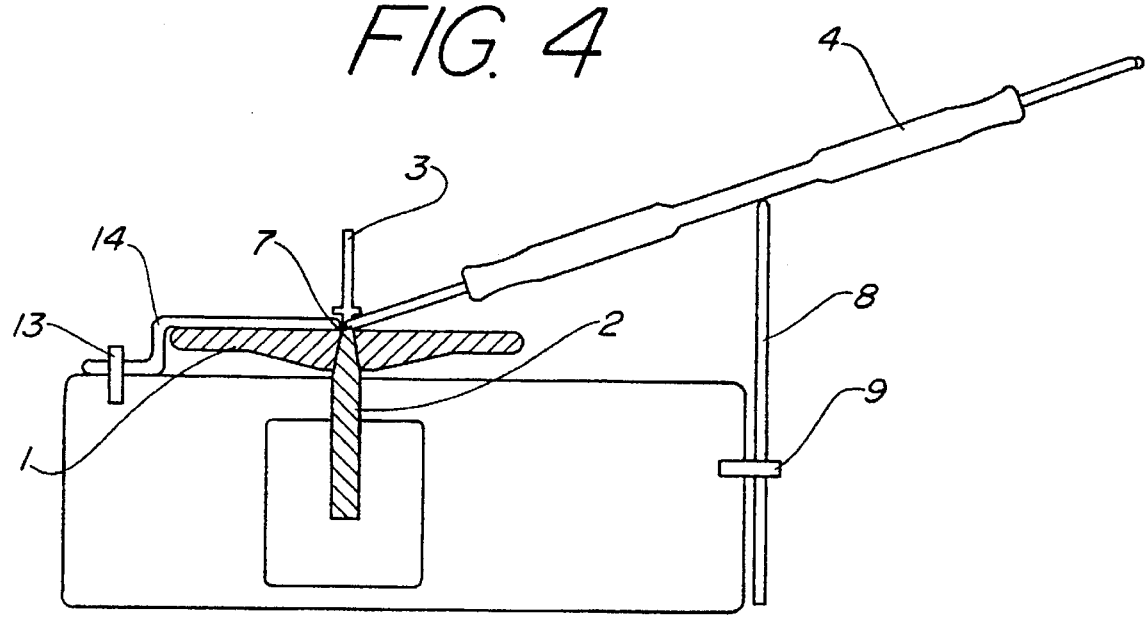
FIG. 4 shows the sharpener displayed from the side, an instrument to be sharpened being placed on the outer facet of the cutting angle, the surface making up the clearance angle. The instrument is supported by a support sheet that is activating the direction of rotation.
Figure 6:
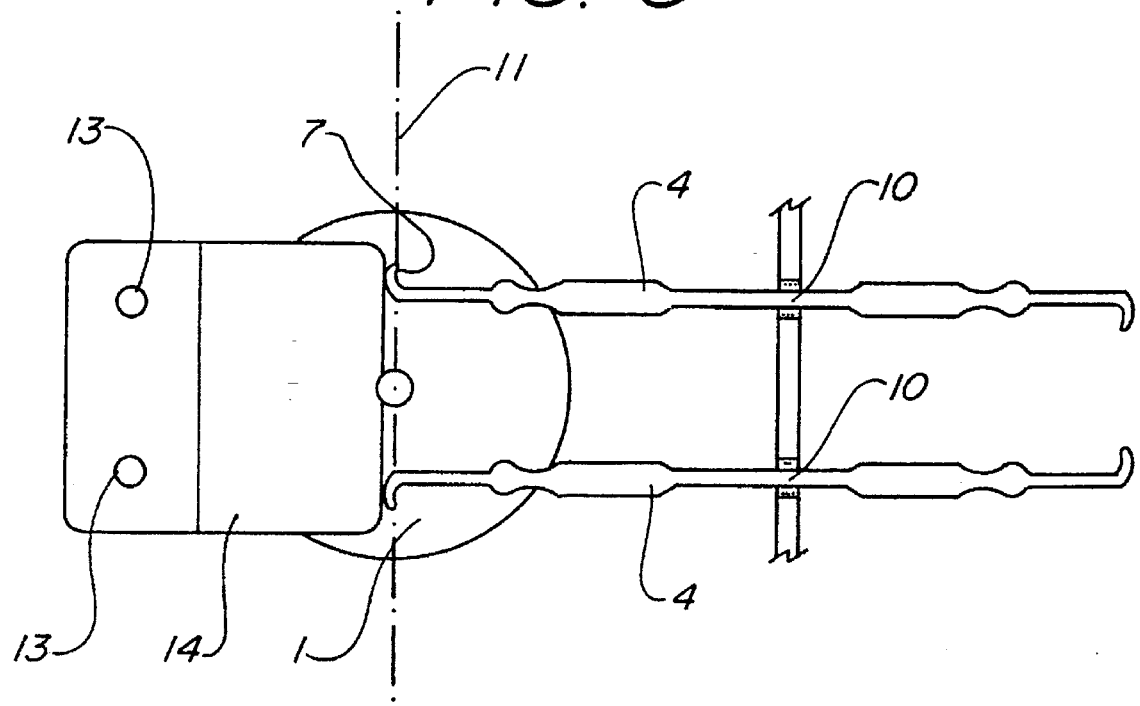
FIG. 6 shows the grinding disk seen from above with the instrument placed for outer grinding the grinding direction is chosen is chosen individually.

There are various ways in which the instrument can be supported in order to carry out the grinding action, any of which would be well within the knowledge of one skilled in the art and all of which would be embraced within the present invention. For example, the handle of the instrument could be supported in a support point 10 on a support sheet 8 as shown in FIGS. 4 and 6 or as shown in U.S. Pat. No. 1,556,471 issued to Andrus. The inner cutting edge of the instrument 4 is positioned against the radiused outer grinding periphery of the grinding disk 1 as shown in FIGS. 1 and 2. It is obvious that with only one fixed support point 10, the inner curved cutting edge of the instrument 4 could be placed against the periphery of the grinding disk 1 at any point on the periphery. If the instrument 4 were, for example, positioned above the grinding disk 1 along a radial line, the cutting edge would be ground flat since the cutting edge would contact the periphery of the grinding disk 1 at a right angle. But if the instrument 4 were positioned so that it contacted the grinding periphery at any other point on the periphery the cutting edge would be ground at some other angle. With only one fixed point supporting the instrument 4, however, the selection of the particular angle would obviously be a matter of chance and the skill of the operator. The significance of the present invention is the provision of another point to fix the position of the instrument 4 with respect to the grinding disk 1, and in particular the relationship of the cutting edge of the instrument 4 to a tangent to the periphery of the grinding disk 1. Consider an instrument 4 supported on a fixed support point 10 on a support sheet 8. Next consider an axle extension 3 of some particular diameter. If the instrument 4 is placed in the support point 10 and rested against the axle extension 3, then clearly the inner cutting edge of the instrument 4 must touch the periphery of the grinding disk 1 at a particular point which is determined by the diameter of the axle extension 3. The particular point on the periphery will produce a particular wedge angle 5 on the inner cutting edge of the instrument, the particular wedge angle 5 being dependent on the angle of the longitudinal axis of the instrument 4 relative to the tangent to the periphery of the grinding disk 1 at the point which the cutting edge touches. Likewise, it is clear that changing the diameter of the axle extension 3 must necessarily change the point on the periphery of the grinding disk where the cutting edge of the instrument touches, which results in a different angle between the longitudinal axis of the instrument 4 and the tangent to the periphery of the grinding disk 1 and therefore produces a different wedge angle 5 on the instrument.

The illustration given above is not limiting to the manner in which the present invention might function. For example, rather than resting the handle of the instrument 4 in a support point 10 on the support sheet 8, means may be provided for holding the cutting edge of the instrument 4 at a fixed point on the periphery of the grinding disk 1. A simple stop of the type described and shown in FIGS. 4, 5, and 6 may be adapted to the task of holding the cutting edge at a fixed point relative to the periphery of the grinding disk. Then the instrument 4 may be rested against the axle extension 3 where a particular diameter establishes an angle of the longitudinal axis of the instrument with respect to a tangent to the point on the periphery where the cutting edge is placed and therefore alters the angle of the cutting edge of the instrument with respect to the tangent to the periphery of the grinding disk. Again, the diameter of the axle extension determines a particular angular relationship between the cutting edge of the instrument 4 and a tangent to the grinding periphery of the grinding disk 1. A different diameter of the axle extension 3 determines a different angular relationship. Furthermore, a skilled operator may simply use the axle extension 3 as a guide to manually achieve a degree of reproducibility in sharpening the wedge angle 5; e.g., by resting the instrument 4 against the axle extension 3 and holding the instrument parallel to some reference, thereby allowing the axle extension 3 to determine the displacement of the instrument away from the center of the grinding disk.

Figure 5:
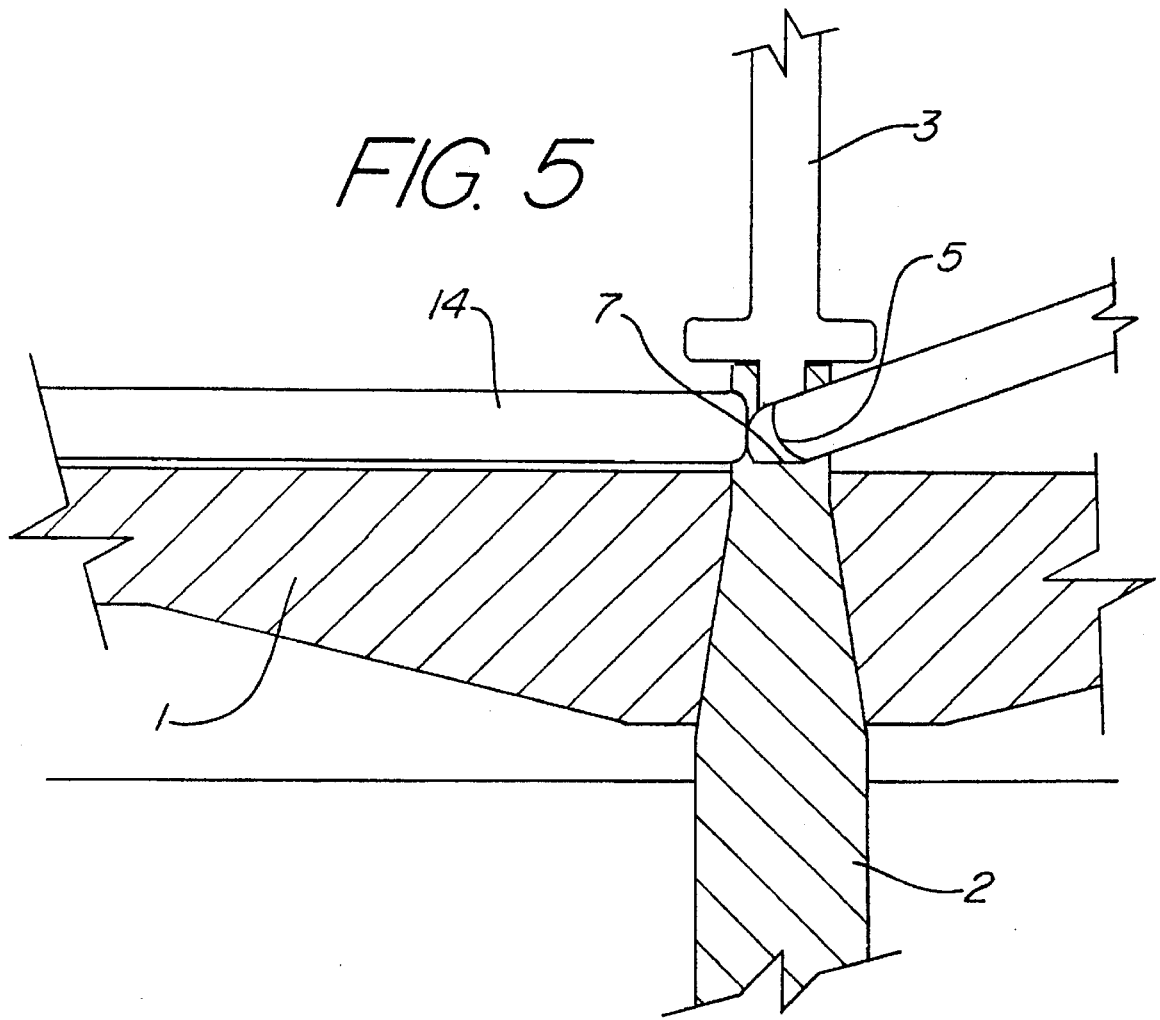
FIG. 5 shows an enlargement of the same as FIG. 4, and the cutting edge is placed in the diagonal line, when the instrument is placed against the diagonal stop.

In addition to the curved inner face of the tip of the instrument 4, the tip has outer cutting edges which must also be sharpened. FIGS. 4, 5, and 6 illustrate the manner in which the outer cutting edge 7 of the instrument 4 may be sharpened on the present invention. The instrument 4 is supported at support points 10 on a support sheet 8 and the tip of the instrument is held against a diagonal stop 14. The diagonal stop 14 is fixed above the surface of the grinding disk 1 by points of fixation 13 so that the diagonal stop 14 holds the cutting edge of the instrument above the diagonal line 11 of the grinding disk 1 at a chosen vertical angle with respect to the horizontal surface of the grinding disk 1. The diagonal line 11 is a line along the diameter of the grinding disk 1 which is parallel to the support sheet 8. The outer cutting edge 7 of the instrument 4 is placed against the surface of the grinding disk 1 for sharpening.

As shown in FIG. 4, the support sheet 8 is attached to sensor 9 which activates the direction of rotation of the grinding disk 1. As shown in FIG. 6, the instrument 4 may be placed in either of two support points 10 on opposite sides of the grinding disk 1. Further as illustrated in FIG. 6, the instrument 4 being sharpened is placed such that the outer cutting edge is placed oppositely depending on which side of the grinding disk 1 the instrument 4 is placed. When the instrument 4 is placed in one of the support points 10, the weight on the support sheet 8 activates the sensor 9 which determines the correct direction of rotation of the grinding disk 1 so as to avoid the formation of burrs on the cutting edge of the instrument 4.

I claim:

1. In a sharpening machine for sharpening the cutting edge of an instrument having a curved inner cutting edge characterized by a radius of curvature and a wedge angle, the sharpening machine being of the type having a rotatable grinding disk with an upward facing grinding surface and mounted on a vertical driving shaft having an axis of rotation, the improvement comprising a support sheet for supporting the instrument at a chosen angle to the grinding surface of the grinding disk when the cutting edge of the instrument is placed on the diagonal line of the grinding disk, a grinding periphery of the grinding disk characterized by a vertical cross section having a radius of curvature that is shorter than the radius of curvature of the curved inner cutting edge of the instrument and against which the curved inner cutting edge of the instrument is placed for grinding the wedge angle, and a support whereby the longitudinal axis of the instrument is supported radially away from the axis of rotation of the driving shaft.

2. The improvement of claim 1, wherein said support comprises an axle extension extending above the grinding surface of the grinding disk and characterized by a diameter and against which the instrument is supported by an offset distance equal to half of said diameter of said axle extension whereby said longitudinal axis of said instrument is supported at a horizontal angle to a tangent to the grinding periphery of the grinding disk when the curved inner edge of the instrument is placed against the grinding periphery of the grinding disk.

3. The improvement of claim 2, further comprising a hub bore in the grinding disk for mounting said axle extension as an extension of said driving shaft.

4. The improvement of claim 3, wherein said axle extension is demountably mounted to said hub bore.

5. The improvement of claim 4, wherein said hub bore of said grinding disk has a conically divergent portion toward an under side of said grinding disk and further wherein said driving shaft further comprises an upwardly oriented end part having a complementary shape to said cortically divergent portion of said hub bore whereby said grinding disk is demountably mounted onto said driving shaft.

6. The improvement of claim 5, further comprising a diagonal stop mounted above said upward facing grinding disk surface of said grinding disk and along said diagonal line of said grinding disk and a support point on said support sheet for supporting the instrument in contact with said grinding surface and said diagonal stop whereby an outer cutting edge of the instrument may be sharpened against said grinding surface.

7. The improvement of claim 6, wherein said support sheet comprises at least two support points for receiving the handle of the instrument and further comprising means operatively connected to said support sheet for activating the direction of rotation of said grinding disk.

* * * * *

UNITED STATES PATENT AND TRADEMARK OFFICE
CERTIFICATE OF CORRECTION

PATENT NO. : 5,655,957
DATED : August 12, 1997
INVENTOR(S) : Lystager, Gregers

It is certified that error appears in the above-identified patent and that said Letters Patent is hereby corrected as shown below:

On the title page, under the heading "U.S. PATENT DOCUMENTS", after the line "1,556,471 10/1925 Andrus ...... 451/549", insert the new line, --1,659,687 2/1928 Hart--.

On the title page, following the line

"5,331,774 7/1994 Domenella ......451/45", insert the new heading, --FOREIGN PATENT DOCUMENTS--, and following the new heading insert the line, --3934365 2/1991 Germany--.

Signed and Sealed this

Twenty-fourth Day of November, 1998

*Attest:*

BRUCE LEHMAN

*Attesting Officer*   *Commissioner of Patents and Trademarks*